United States Patent [19]
Fukuyama et al.

[11] Patent Number: 6,019,104
[45] Date of Patent: Feb. 1, 2000

[54] METHOD FOR THE TREATMENT OR PREVENTION OF RESTENOSIS ASSOCIATED WITH CORONARY INTERVENTION

[75] Inventors: Juichi Fukuyama, Hotaka-machi; Keiji Miyazawa, Tokyo-to; Shuichiro Hamano, Matsumoto; Arao Ujiie, Toyoshina-machi, all of Japan

[73] Assignee: Kissei Pharmaceutical Co., Ltd., Japan

[21] Appl. No.: 08/774,418

[22] Filed: Dec. 30, 1996

[51] Int. Cl.[7] ...................................................... A61B 19/00
[52] U.S. Cl. .............................................. 128/898; 514/535
[58] Field of Search ................................... 514/535, 563, 514/930; 128/898; 549/441

[56] References Cited

U.S. PATENT DOCUMENTS

| | | | |
|---|---|---|---|
| 3,940,422 | 2/1976 | Harita et al. ............................. | 549/411 |
| 4,070,484 | 1/1978 | Harita et al. ............................. | 514/563 |
| 4,337,270 | 6/1982 | Noda et al. .............................. | 514/535 |
| 5,385,935 | 1/1995 | Tamai et al. ............................. | 514/535 |

OTHER PUBLICATIONS

British Journal of Pharmacology 118, 915–922 (1996) "Anti proliferative and c–myc mRNA Suppressive effects of tranilaston . . . ".

Can. J. Physiol. Pharmacol. 74, 80–84 (1996) "Inhibitory effects of tranilast on proliferation, migration, and collagen synthesis of human vascular . . . ".

Atherosclerosis 118, 213–221 (1995) "Inhibition of PDG-F–and TGF–Bi–induced collagen synthesis migration, and proliferation by tranilast in vascular smooth muscle cells from . . . ".

Ohyouyakuri 50 (5), 539–548 (1995) "Suppressive effect of an anti–allergic Drug, Tranilast, on the Vascular Intimal . . . ".

European Journal of Pharmacology, 295, 221–227 (1996) "Tranilast suppresses intimcl hyperplasia . . . ".

Jpn. J. Pharmacol. 70, 321–327 (1996) "Tranilast Suppresses Intimcl Hyperplasia in the balloon injury model and cuff . . . ".

*Primary Examiner*—Mickey Yu
*Assistant Examiner*—Kelly O'Hara
*Attorney, Agent, or Firm*—Depaoli & Frenkel, PC

[57] ABSTRACT

A method for treating patients to inhibit restenosis associated with coronary intervention, which comprises administering compounds of the class of aminobenzoic acids, specifically 2-(3,4-dimethoxy-cinnamoyl)-aminobenzoic acid or its pharmaceutically acceptable salt at a dosage which is sufficient to maintain the plasma concentration at about 100μ molar for a period of time of less than three months.

4 Claims, No Drawings

METHOD FOR THE TREATMENT OR PREVENTION OF RESTENOSIS ASSOCIATED WITH CORONARY INTERVENTION

FIELD OF THE INVENTION

The present invention relates to a new method for the treatment or prevention of restenosis associated with coronary interventions.

More particularly, the present invention relates to a new method for the treatment or prevention of restenosis associated with coronary interventions by using a pharmaceutical formulation containing 2-(3,4-dimethoxy-cinnamoyl) aminobenzoic acid (hereinafter referred to as Tranilast) represented by the following formula (I) or a pharmaceutically acceptable salt thereof as an active ingredient.

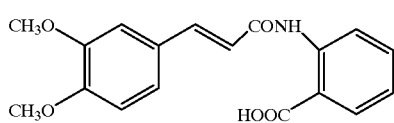

(I)

Illustrative of pharmaceutically acceptable salts are inorganic salts such as sodium or calcium salt, or organic salts formed with amines such as morpholine, piperidine, arginine, and the like.

As examples of coronary interventions in the present invention, Percutaneous Transluminal Coronary Angioplasty (PTCA), Direction coronary Atherectomy (DCA) and Stent can be illustrated.

BACKGROUND OF THE INVENTION

1. Technical Field of the Invention

Coronary intervention is a surgical approach to the treatment of ischemic heart diseases such as angina pectoris and myocardial infarction. Coronary intervention technically involves mechanical revascularization of a stenosed lesion in a coronary artery by means of a balloon catheter, an atherectomy catheter and the like. As a consequence, coronary intervention often causes restenosis due to damaged vessel walls.

2. Description of the Invention

Tamai et al found that Tranilast reduces the incidence of restenosis associated with coronary intervention, and provided a method for the prevention or treatment of restenosis associated with coronary intervention (U.S. Pat. No. 5,385,935). Said method comprises administering Tranilast or a pharmaceutically acceptable salt thereof in a daily dose of about 300–1000 mg, preferably about 300–600 mg, for a treatment period of about 3–6 consecutive months after coronary intervention.

However, it now has been found that the treatment or prevention of restenosis associated with coronary intervention can be accomplished with a different dosage and administration term than is specified in U.S. Pat. No. 5,385,935.

SUMMARY OF THE INVENTION

An object of the present invention is to provide a clinically more favorable method for the treatment or prevention of restenosis associated with coronary interventions by administering a pharmaceutical formulation containing Tranilast or a pharmaceutically acceptable salt thereof as an active ingredient.

Other objects, features and advantages of the present invention will become apparent from the following description and examples.

DETAILED DESCRIPTION OF THE INVENTION

The present invention is directed to an improved method for administering a safe and effective dosage of Tranilast for the treatment or prevention of restenosis associated with coronary intervention.

M. Nobuyoshi conducted pathological observations on coronary vessels of 7 patients who died within 3 months after coronary intervention (PTCA), and reported that excessive proliferation of vascular smooth muscle cells (hereinafter referred to as VSMCs) could be observed but excessive production of collagen could not be observed (PTCA, pages 15–21, published by IGAKUSHOIN, 1988). This report suggests that proliferation of VSMCs plays a key role in restenosis associated with coronary interventions.

For purposes of the present invention, it was concluded that a drug concentration in human plasma which prevents proliferation of VSMCs is a desirable method for the treatment or prevention of restenosis associated with coronary intervention. This was confirmed by clinical tests.

It was found that Tranilast significantly prevents proliferation of human VSMCs at 100 micromolar concentration (100 $\mu$M) in human plasma (Fukuyama et al, Canadian Journal of Physiology and Pharmacology, vol. 74, No. 1, pp. 80–84, 1996). It was demonstrated that proliferation of VSMCs in humans can be prevented by administering Tranilast at a plasma concentration of about 100 $\mu$M.

Data was obtained from clinical studies in which Tranilast was administered to three healthy adult humans in a dose of 2.5 mg/kg three times per day for a period of five days. It was confirmed that when Tranilast was administered in a dose of 2.5 mg/kg three times per day, the plasma concentration of Tranilast reached a steady state of about 18.7–27.4 $\mu$g/ml (about 57–84 $\mu$M) on the 2nd day after the first administration.

Thus, it was demonstrated that restenosis associated with coronary interventions can be treated or prevented by administering Tranilast so as to maintain a plasma concentration of about 100 $\mu$M which is effective for preventing the proliferation of human VSMCs. For example, in the case of patients weighing 60 kg, Tranilast was administered in a dose of about 500–790 mg per day in order to obtain a plasma concentration of about 100 $\mu$M which prevents or treats restenosis associated with coronary intervention.

Since absorption of Tranilast varies depending on the weight and sex and age of the patients, the severity of the condition to be treated, and the like, it is preferable to determine a daily dose of Tranilast so as to maintain a plasma concentration of about 100 $\mu$M in view of the status of patients. A plasma concentration which prevents proliferation of VSMCs varies depending on the nature of patients. Therefore, a plasma concentration which prevents proliferation of VSMCs, i.e., 100 $\mu$M, has to be a guide for the treatment or prevention of restenosis associated with coronary intervention.

Data also was obtained from clinical studies of patients who were administered a dose of 600 mg of Tranilast per body per day for a period of 8 weeks to 3 months after coronary interventions (PTCA), and it was confirmed that the incidence of restenosis after coronary intervention (PTCA) was less than 20% with drug treatment. When a placebo was administered to patients, the incidence of restenosis was about 50%.

Ueda et al conducted pathologic studies by angiography on cardiovascular vessels after coronary intervention, and reported that a large proliferation of VSMCs occurs at about 12 days after coronary intervention [Kokyu to Junkan (RESPIRATION AND CIRCULATION), vol. 43, No. 3, pp. 257–262, 1995].

Tamai et al proposed that Tranilast has to be administered in a daily dose of 300–1000 mg for a period of about 3–6 consecutive months after coronary intervention. Taking into consideration that proliferation of VSMCs is a critical factor in restenosis associated with coronary intervention, and that proliferation of VSMCs occurs at an early stage after coronary intervention, the method proposed by Tamai et al is not the only protocol for the treatment or prevention of restenosis associated with coronary intervention. The data from clinical studies stated above demonstrate that Tranilast has to be administered after coronary intervention in a manner which prevents excessive proliferation of VSMCs. It is not necessary to administer Tranilast for a period of more than 3 months, since in accordance with the present invention a shorter treatment period is effective for the prevention or treatment of restenosis.

Tranilast and pharmaceutically acceptable salts thereof of the present invention are known compounds and can be prepared according to standard processes, such as the method described in U.S. Pat. No. 4,623,724.

When Tranilast or a pharmaceutically acceptable salt thereof is employed therapeutically, it can be administered in appropriate dosage forms, such as powder, granules, tablets, capsules, dry-syrups, plasters, suppositories, injectable solutions, and the like.

A Tranilast pharmaceutical composition can be formulated by admixing suitable carriers such as excipients, disintegrators, binders, brighteners, and the like, and prepared in accordance with conventional molding methods and dosage forms.

The present invention is further illustrated in more detail by way of the following Examples.

EXAMPLE I

This Example demonstrates the effect of Tranilast on proliferation and migration in culture of human vascular smooth muscle cells (VSMCs).

A. Cell Culture

Newborn human aortic smooth muscle cells at the fourth passage culture were provided by Kurabo (Osaka, Japan). Confluent VSMCs were subcultured at a 1:5 split ratio in DMEM supplemented with 10% FBS. VSMCs were used within passages 5–10 and were characterized as smooth muscle by morphologic criteria and by expression of smooth muscle α-actin. The cells were negative in mycoplasma assays.

B. Cell Proliferation Assay

The cell proliferation assay was performed by counting the number of cells. First, VSMCs was seeded at a density of $3 \times 10^3$ cells/cm$^2$ in DMEM supplemented with 10% FBS in 25 cm$^2$ tissue culture flasks. The next day, the medium was discarded, and fresh DMEM (10% FBS) containing various concentrations of Tranilast was added to the cells. Four days after the addition of Tranilast, the number of cells was determined with a hematocytometer.

C. Measurement of DNA Synthesis

Cells were grown to confluence in 96-well tissue culture dishes, and the growth was arrested for 48 hours in a serum-free medium consisting of DMEM supplemented with 5 μg/ml insulin, 5 μg/ml transferrin, and 5 ng/ml selenium (ITS). The DMEM-ITS medium was employed to maintain the VSMCs in a quiescent but not catabolic state, a condition that resembles that of healthy cells in the normal arterial wall in vivo (Libby and O'Brien 1983). The DMEM-ITS medium was then removed, and fresh DMEM containing a growth factor was added to the quiescent cells. The cells were subsequently incubated for 20 hours in the absence or presence of Tranilast. The cells were then incubated with [$^3$H]thymidine(46 kBq/ml) for 2 hours in the absence or presence of Tranilast. Next, ice-cold 10% trichloroacetic acid was added to each well, and the plates were kept at 4° C. for 10 minutes. Trichloroacetic acid insoluble materials were then harvested onto Unifilter plates (GF/B 96, Packard Instrument, Meriden, Conn.) with a cell harvester. The extent of [$^3$H]thymidine incorporation was determined by scintillation counting.

D. Migration Assay

The migration of cells was assayed by a modified Boyden's chamber method using a 96-well Boyden chamber apparatus (Neuroprobe Inc., Cabin John, Md.) (Grotendorst et al 1982). Chemoattractant (PDGF-BB) was first diluted in DMEM with or without Tranilast and then loaded into the lower wells of the Boyden chamber. The wells were subsequently covered with a standard 8 μm pore filter (Nucleopore Corp., Pleasanton, Calif.) coated with type I collagen. The cell suspensions ($1 \times 10^4$ cells) in DMEM containing 0.1% bovine serum albumin (BSA) with or without Tranilast were then loaded into the upper wells of the chamber, after which the chamber was incubated for 4 hours at 37° C. in an atmosphere of 95% air and 5% $CO_2$. Nonmigrated cells on the upper surface were scraped off. The filters were then fixed in methanol and strained with Diff-Quick staining solution (International Reagent Corp., Kobe, Japan). The number of VSMCs per 400× high power field (HPF) that had migrated to the lower surface of the filters was then determined microscopically. Four HPFs were counted per well, and the values were averaged.

E. Results (1) Effect of Tranilast on human VSMCs proliferation

Tranilast significantly inhibited the proliferation of human VSMCs in a 100μ molar concentration.

(2) Effect of Tranilast on PDGF-BB-induced DNA Synthesis in Quiescent Human VSMCs Tranilast significantly inhibited DNA synthesis in quiescent human VSMCs that were stimulated with 50 ng/ml PDGF-BB in a 100μ molar concentration.

(3) Effect of Tranilast on PDGF-BB-induced Migration in Human VSMCs

Tranilast significantly inhibited the VSMCs migration elicited by 50 ng/ml PDGF-BB in a 100μ molar concentration.

EXAMPLE II

This Example demonstrates a sufficient dosage period of Tranilast for treatment or prevention of restenosis associated with PTCA surgery.

Two hundred eighty eight patients had angina pectoris or myocardial infarction and who underwent successful elective PTCA (including repeat PTCA) in their significant stenotic lesion(s) participated in this study. These patients were divided into two groups, and all groups did not differ significantly in sex, age and body weight; first group received placebo (hereinafter identified P group), second group received Tranilast in a daily dose of 600 mg (hereinafter identified T group).

These drugs were administered within 3 consecutive months after PTCA.

And coronary angiography was performed immediately before and immediately after PTCA, and 3 months (or at the time of withdrawal) after the completion of drug administration.

Two hundred fifty-six lesions of two hundred thirty-two patients whose PTCA was successful and had not withdrawn participated in efficacy evaluation, and each lesion was evaluated based on the change in stenosis using the following grades.

No restenosis: The loss in the stenotic region dilated by PTCA was less than 50% of the gain (loss/gain <50%).
Restenosis: The loss in the stenotic region dilated by PTCA was not less than 50% of the gain loss/gain ≧50%).

| A. Patient Background (188 cases used for analysis of efficacy) | | | | |
|---|---|---|---|---|
| Item | Classification | P group (114 Ps) | T group (118 Ps) | Test |
| Sex | Male | 86 | 94 | NS |
| | Female | 28 | 24 | P = 0.529 |
| Age | <65 yrs old | 58 | 68 | NS |
| | 65 yrs old ≦ | 13 | 17 | P = 0.302 |
| | Mean ± S.D. | 63.8 ± 0.8 | 62.5 ± 0.9 | NS P = 0.346 |
| Body weight | Mean ± S.D | 60.8 ± 0.8 | 60.8 ± 0.8 | NS P = 0.936 |

| B. Baseline characteristics of lesions (subjected to efficacy evaluation) | | | | |
|---|---|---|---|---|
| Item | Classification | P group (126 Ls) | T group (130 Ls) | Test |
| PTCA | Initial PTCA | 85 | 100 | + |
| | Repeat PTCA | 41 | 30 | P = 0.096 |
| Branch | RCA | 40 | 40 | NS |
| | LAD | 55 | 61 | P = 0.838 |
| | LCX | 31 | 29 | |
| Type | type A | 16 | 11 | NS |
| | type B | 107 | 117 | P = 0.407 |
| | type C | 3 | 2 | |
| | Length of Lesion (mm) Mean ± S.D | 6.1 ± 0.4 (n = 67) | 6.3 ± 0.3 (n = 64) | + P = 0.097 (n = 63) |

| C. Results | | | |
|---|---|---|---|
| Subst. Admin. Term | P group | T group | Test |
| (1) Restenosis rate by lesion | | | |
| <8 weeks rate | (3 Ls) 33.3% | (14 Ls) 42.9% | NS P = 1.0000 |
| 8 weeks ≦ rate | (127 Ls) 44.1% | (112 Ls) 18.8% | *** P = 0.0000 |
| (2) Restenosis rate by patient | | | |
| <8 weeks rate | (2 Ps) 50.0% | (14 Ps) 42.9% | NS P = 1.0000 |
| 8 weeks ≦ rate | (112 Ps) 47.3% | (104 Ps) 20.2% | *** p = 0.0000 |

What is claimed is:

1. A method for the treatment or prevention of restenosis associated with coronary intervention in a human patient, which comprises administering to the patient 2-(3,4-dimethoxy-cinnamoyl)aminobenzoic acid or a pharmaceutically acceptable salt thereof in a daily dose which is sufficient to maintain a plasma concentration of 2-(3,4-dimethoxy-cinnamoyl)aminobenzoic acid or a pharmaceutically acceptable salt thereof at about $100\mu$ molar concentration for a treatment period of less than about 3 months after coronary intervention; wherein the proliferation of human vascular smooth muscle cells is prevented by the treatment.

2. A method in accordance with claim 1 wherein the coronary intervention is Percutaneous Transluminal Coronary Angioplasty.

3. A method in accordance with claim 1 wherein the coronary intervention is Direction Coronary Atherectomy.

4. A method in accordance with claim 1 wherein the coronary intervention is Stent.

* * * * *